US012612613B2

(12) United States Patent
Adachi et al.

(10) Patent No.: US 12,612,613 B2
(45) Date of Patent: Apr. 28, 2026

(54) D-MANNOSE ISOMERASE AND PRODUCTION METHOD OF D-FRUCTOSE

(71) Applicant: YAMAGUCHI UNIVERSITY, Yamaguchi (JP)

(72) Inventors: Osao Adachi, Yamaguchi (JP); Toshiharu Yakushi, Yamaguchi (JP); Naoya Kataoka, Yamaguchi (JP); Kazunobu Matsushita, Yamaguchi (JP)

(73) Assignee: YAMAGUCHI UNIVERSITY, Yamaguchi (JP)

( * ) Notice: Subject to any disclaimer, the term of this patent is extended or adjusted under 35 U.S.C. 154(b) by 371 days.

(21) Appl. No.: 18/271,132

(22) PCT Filed: Dec. 28, 2021

(86) PCT No.: PCT/JP2021/048791
§ 371 (c)(1),
(2) Date: Jul. 6, 2023

(87) PCT Pub. No.: WO2022/149542
PCT Pub. Date: Jul. 14, 2022

(65) Prior Publication Data
US 2024/0052333 A1 Feb. 15, 2024

(30) Foreign Application Priority Data

Jan. 6, 2021 (JP) ................................. 2021-001146

(51) Int. Cl.
| | |
|---|---|
| *C12N 9/90* | (2006.01) |
| *C07H 1/00* | (2006.01) |
| *C07H 1/06* | (2006.01) |
| *C12N 11/02* | (2006.01) |
| *C12P 19/02* | (2006.01) |
| *C12P 19/24* | (2006.01) |

(52) U.S. Cl.
CPC ................ *C12N 9/90* (2013.01); *C12N 11/02* (2013.01); *C12P 19/02* (2013.01); *C12Y 503/01007* (2013.01)

(58) Field of Classification Search
CPC .. C12N 9/90; C12N 1/00; C12P 19/24; C07H 1/00; C07H 1/106
See application file for complete search history.

(56) References Cited

U.S. PATENT DOCUMENTS

| | | | |
|---|---|---|---|
| 4,734,366 A | 3/1988 | Arena et al. |
| 6,673,581 B1 | 1/2004 | Koizumi et al. |
| 8,227,232 B2 | 7/2012 | Izumori et al. |

FOREIGN PATENT DOCUMENTS

| | | |
|---|---|---|
| JP | 2020-146020 A | 9/2020 |
| WO | 00/65072 A1 | 11/2000 |
| WO | 2008/062569 A1 | 5/2008 |

OTHER PUBLICATIONS

England et al., J.B.C., 240(6), 2297-2301, 1965.*
Adachi et al., Bioscience, Biotechnology, and Biochemistry , 2022, vol. 86, No. 7, 938-948.*
Gonzalez et al., "Mannose impairs tumour growth and enhances chemotherapy," Nature, 563: 719-723 (2018).
Takasaki et al., "Studies on the Isomerization of Sugars by Bacteria Part VII. Constitutive Production of Mannose Isomerase by *Xanthomonas* species," Agricultural and Biological Chemistry, 28(9): 601-604 (1964).
Takasaki et al., "Studies on the Isomerization of Sugars by Bacteria Part VII. Constitutive Production of Mannose Isomerase by Xanthomonas rubrilineans S-48," Agricultural and Biological Chemistry, 28 (9): 605-609 (1964).
Hirose et al., "Purification and Characterization of Mannose Isomerase from Agrobacterium radiobacter M-1," Bioscience, Biotechnology, and Biochemistry, 65(3): 658-661 (2001).
Takasaki, "Enzymatic conversion of glucose to fructose under acidic condition," Bioscience, Biotechnology, and Biochemistry, 71(6): 621-624 (1997) (see partial English translation).
Takasaki, "Development of Thermostable and/or Acid Stable alpha-Amylase, Glucose Isomerase and Mannose Isomerase," Journal of Japanese Society for Food Science and Technology, 48(2), 150-156 (2001) (see partial English translation).
Adachi et al., "Discovery of membrane-bound D-mannose isomerase and its application to high fructose syrup production," Annual Meeting of the Japan Society for Bioscience, Biotechnology, and Agrochemistry 2021, 4C01-13.
International Search Report issued in corresponding International Patent Application No. PCT/JP2021/048791 dated Feb. 15, 2022.
Allenza et al., "Conversion of Mannose to Fructose by Immobilized Mannose Isomerase from Pseudomonas cepacia", Applied Biochemistry and Biotechnology vols. 24 and 25, 1990, pp. 171-182.
Extended European Search Report issued in corresponding European Patent Application No. 21917762.3, dated Dec. 13, 2024.

* cited by examiner

*Primary Examiner* — Maryam Monshipouri
(74) *Attorney, Agent, or Firm* — Morgan, Lewis & Bockius LLP

(57) ABSTRACT

The present invention has an object to provide a D-mannose isomerase of membrane-bound form having the optimal reaction pH in acidic region. The membrane-bound D-mannose isomerase derived from acetic acid bacteria is produced. The acetic acid bacteria preferably belong to the genera of Acetobacter, Gluconobacter, or Gluconacetobacter. Furthermore, the membrane-bound D-mannose isomerase from the acetic acid bacteria is used to produce D-fructose from D-mannose.

15 Claims, 4 Drawing Sheets

[FIG.1]
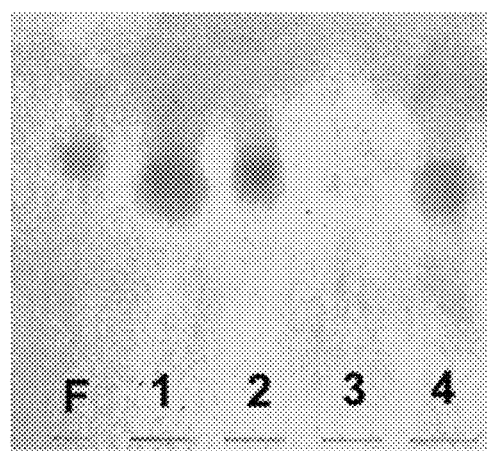
[FIG.2]
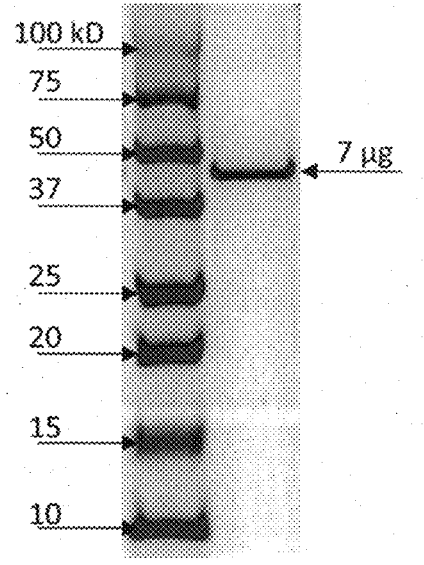

[FIG.3]
Measurement of Molecular Weight of MMI
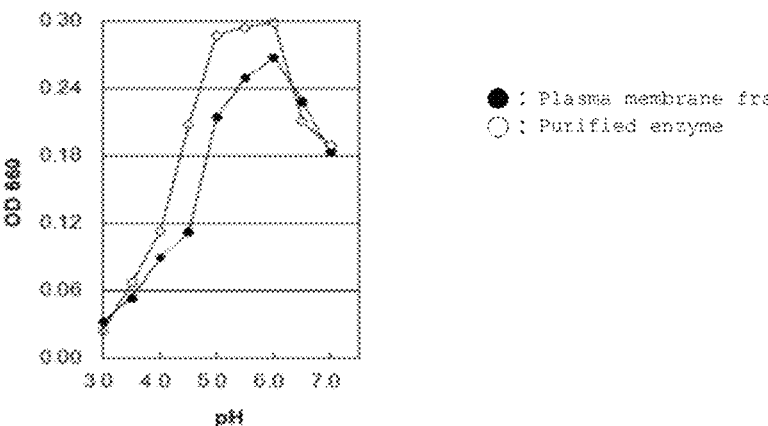
[FIG.4]
● : Plasma membrane fraction
○ : Purified enzyme

[FIG.5]

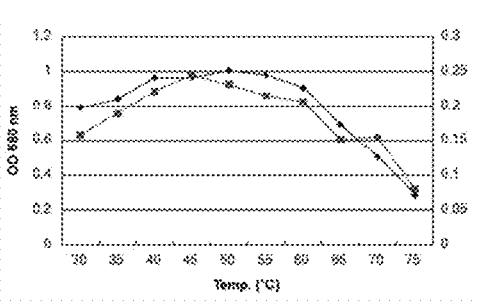

■ : Plasma membrane fraction (left ordinate)
◆ : Purified enzyme (right ordinate)

[FIG.6]

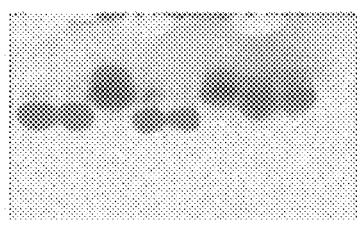

1 2 3 4 5 6 7 8

1 : Reaction solution of D-xylose and enzyme
2 : Standard D-xylose
3 : Standard D-xylulose
4 : Reaction solution of arabinose and enzyme
5 : Standard D-arabinose
6 : Standard D-ribulose
7 : Reaction solution of D-ribose and enzyme
8 : Standard D-ribose

[FIG.7]

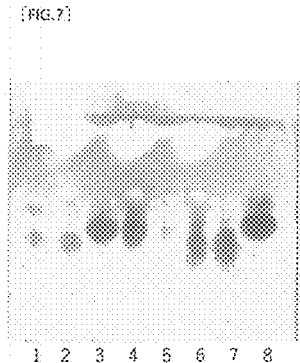

1 2 3 4 5 6 7 8

1 : Standard D-arabinose
2 : Reaction solution of D-glucose and enzyme
3 : Standard D-fructose
4 : Reaction solution of D-mannose and enzyme
5 : Standard D-mannose
6 : Reaction solution of D-galactose and enzyme
7 : Standard D-galactose
8 : Standard D-tagatose

[FIG.8]
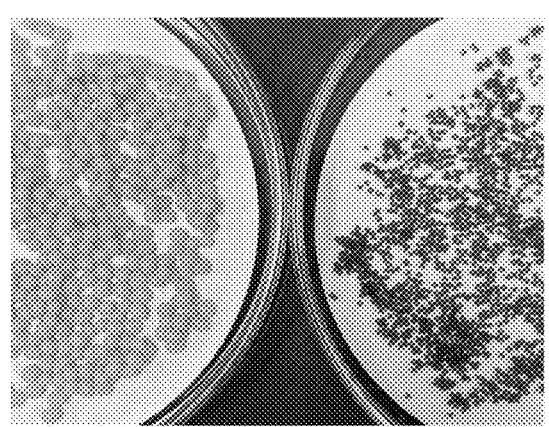

D-MANNOSE ISOMERASE AND PRODUCTION METHOD OF D-FRUCTOSE

TECHNICAL FIELD

The present invention relates to a membrane-bound D-mannose isomerase (membrane-bound D-mannose isomerase) or a method of producing D-fructose (fructose) from D-mannose.

BACKGROUND ART

Konjac mannan, a main component of konjac taro, is polysaccharide containing D-mannose and D-glucose joined together by β-1,4-glycoside linkage, and is indigestible, causing its limited use to only traditional production of konjac food (jelly devil's tongue) with least calories. Under such circumstances, the inventors have pursued researches for the purpose of providing application of konjac taro with additional value and further effective utilization of konjac taro. Consequently they disclosed a method of konjac taro koji production from konjac taro. A complete hydrolysis technology for konjac taro polysaccharides was realized for the first time with use of such konjac taro koji (see Patent Literature 1). The konjac taro koji catalyzes a complete hydrolysis of konjac taro into a carbohydrate resource, thus enhancing expectation for contribution to improve food self-sufficiency in Japan. Furthermore, the konjac taro hydrolysate is expected to be utilized as digestible food with higher calories.

D-mannose contained in the konjac taro hydrolysate is: (1) integrated into the glycolysis system in the body as much as galactose and then consumed, and thus known to be utilized as health dietary, and (2) known to be utilized as a tumor growth suppressor (see Non Patent Literature 1).

Meanwhile, commercial foods or beverages have widely used D-fructose as a sweetener. D-fructose is generally manufactured by a method of isomerizing D-glucose obtained from corn. D-fructose can also be generated by isomerizing D-mannose. There have been several known isomerases for sugars containing D-mannose (see Non Patent Literatures 2-4), and all of these are cytoplasmic origin unexceptionally. Moreover, because of their cytoplasmic origin, their enzyme reactions require mechanical cell disruption and then enzyme extraction from the cells. Furthermore, sugar becomes generally sensitive and labile to alkaline, and generates by-products, such as colored substances, at neutral pH or higher. For these reasons, D-glucose isomerase having, e.g., an optimal reaction pH (hereinafter also referred to as "optimal pH") of 4-6 have also been explored but not found yet. Furthermore, such an enzyme also has been considered to possibly be not existed in view of its reaction mechanism (see Non Patent Literatures 5 and 6). Additionally, D-mannose can be chemically oxidized to D-mannitol, which is then also converted to D-fructose. However, such the reaction consists of two steps, thus creating concerns about complication of the reaction pathway and reduction in D-fructose yield.

CITATION LIST

Patent Literature

PATENT LITERATURE 1: JP 2020-146020 A

Non Patent Literature

NON PATENT LITERATURE 1: Pablo Sierra Gonzalez et al., Nature, 563, 719-723(2018), doi: 10.1038/s41586-018-0729-3

NON PATENT LITERATURE 2: Takasaki et al., Agr. Biol. Chem., 28(9), 601-604 (1964)

NON PATENT LITERATURE 3: Takasaki et al., Agr. Biol. Chem., 28(9), 605-609 (1964)

NON PATENT LITERATURE 4: Hirose et al., Biosci. Biotechnol. Biochem., 65(3), 658-661 (2001)

NON PATENT LITERATURE 5: Takasaki Y., Biosci. Biotechnol. Biochem., 71(6), 621-624 (1997)

NON PATENT LITERATURE 6: Takasaki Y, J. Jpn. Soc. Food Sci. Technol., 48(2), 150-156 (2001)

SUMMARY OF INVENTION

Technical Problem

The present invention is to provide D-mannose isomerase of membrane-bound form having the optimal pH in acidic region.

Solution to Problem

In earnest investigation to solve the problem described above, the inventors focused on acetic acid bacteria used in production of vinegaretc. They discovered D-mannose isomerase derived from the cytoplasmic membrane fraction of acetic acid bacteria, and completed the present invention.

That is, the present invention is as follows.

[1] A membrane-bound D-mannose isomerase derived from the cytoplasmic membrane of acetic acid bacteria.

[2] The membrane-bound D-mannose isomerase according to the item [1] having the following characteristics (a)-(c):

(a) acting on D-mannose to generate D-fructose;

(b) having the optimal reaction pH of 5.0-6.5 under the reaction condition at 50° C.; and (c) having the optimal reaction temperature of 40-65° C. under the reaction condition at pH 6.0 for 30 minutes.

[3] The membrane-bound D-mannose isomerase according to the item [1] or [2], wherein the acetic acid bacteria belong to the genera of *Acetobacter, Gluconobacter,* or *Gluconacetobacter.*

[4] An immobilized enzyme comprising the membrane-bound D-mannose isomerase according to any one of the items [1]-[3] immobilized to a carrier.

[5] A method of producing the membrane-bound D-mannose isomerase comprising culturing acetic acid bacteria in a nutrient medium, and then obtaining bacterial cells, or preparing the cytoplasmic membrane fraction from the bacterial cells thus obtained.

[6] A method of D-fructose production comprising causing the D-mannose isomerase according to any one of the items [1]-[3] or the immobilized enzyme according to the item [4] to act on D-mannose solution.

Advantageous Effects of Invention

The membrane-bound D-mannose isomerase in the present invention is an enzyme bound to the cytoplasmic membrane and has the optimal pH in acidic region, thus allowing stable production of D-fructose with least generation of brown-colored by-products. In addition, use of the membrane-bound D-mannose isomerase in the present invention as an immobilized catalyst enables easy separation or recovery of D-fructose from a reaction mixture. Furthermore, the enzyme is derived from acetic acid bacteria and thus allows utilization of D-fructose. Because acetic acid bacteria are familiar microorganisms having a long history of eating experience for food with high safety.

BRIEF DESCRIPTION OF DRAWINGS

FIG. 1 illustrates results from reacting D-mannose, as a substrate, with cells, cytoplasmic membrane fraction, cytoplasmic fraction, and solubilized enzyme from the cytoplasmic membrane fraction, and then subjecting each of the reaction mixture to TLC analysis in Example 1.

FIG. 2 illustrates results of measuring molecular mass by SDS-PAGE of the purified D-mannose isomerase in Example 4.

FIG. 3 illustrates results of measuring molecular mass of the purified D-mannose isomerase by gel filtration in Example 4.

FIG. 4 illustrates results of examining optimal pH in Example 5.

FIG. 5 illustrates results of examining optimal reaction temperature (hereinafter also referred to as "optimal temperature") in Example 6.

FIG. 6 illustrates results of examining substrate specificity (substrate: C5 sugars) in Example 7.

FIG. 7 illustrates results of examining substrate specificity (substrate: C6 sugars) in Example 7.

FIG. 8 shows a photograph of immobilized cells provided in Example 10.

DESCRIPTION OF EMBODIMENTS

The membrane-bound D-mannose isomerase in the present invention is a membrane-bound D-mannose isomerase (EC 5.3.1.7) derived from acetic acid bacteria, and hereinafter also referred to as "the membrane-bound D-mannose isomerase". The membrane-bound D-mannose isomerase is an enzyme that catalyzes reversible isomerization reaction from D-mannose to D-fructose. Additionally, the immobilized enzyme in the present invention is not particularly limited as long as it is an immobilized enzyme characterized by being immobilized to a carrier; hereinafter it is also referred to as "the immobilized enzyme". Furthermore, the method of producing the membrane-bound D-mannose isomerase in the present invention is not particularly limited, as long as it is a method including culturing acetic acid bacteria in a nutrient medium, and then obtaining bacterial cells, or preparing the cytoplasmic membrane fraction from the bacterial cells thus obtained; hereinafter it is also referred to as "the method of producing the membrane-bound D-mannose isomerase". Furthermore, the method of producing D-fructose (fructose) in the present invention is not particularly limited, as long as it is a method of producing D-fructose catalyzed by membrane-bound D-mannose isomerase or the immobilized enzyme to act on a solution containing D-mannose. Hereinafter, it is also referred to as "the method of producing D-fructose".
(Membrane-Bound D-Mannose Isomerase)

The term "membrane-bound" herein means the D-mannose isomerase being bound to the cytoplasmic membrane. The term "membrane-bound D-mannose isomerase derived from acetic acid bacteria" means a D-mannose isomerase bound to the cytoplasmic membrane of the acetic acid bacteria, or separated or purified from the cytoplasmic membrane of the acetic acid bacteria. The nature of membrane-bound enzyme catalyzed generation of D-fructose by the acetic acid bacteria itself or a membrane fraction obtained from the acetic acid bacteria to act on D-mannose, even without disruption of the acetic acid bacteria. The nature of membrane-bound enzyme also allows maintenance of the enzyme activity stable for a long period.

The optimal pH of the membrane-bound D-mannose isomerase is work at pH 5.0-6.5, preferably pH 5.5-6.0, and more preferably pH 6.0 under the reaction condition at 50° C. Conventional methods of D-glucose isomerization have used isomerases active in alkaline region, but generated brown by-products due to Maillard reaction, etc. at the pH of higher than 8.0. This has led to a need for removing the brown by-products corresponding to a product of interest. By contrast, use of the membrane-bound D-mannose isomerase eliminates the concern about generating the brown by-products, and has no need of the step of removing the by-products.

Furthermore, as shown in the Non Patent Literature 5, saccharification has formerly been performed in acidic region, followed by D-glucose isomerization by a reaction in alkaline region for production of isomerized sugar from corn for the purpose of adjusting the reaction condition to the optimal pH of the isomerase. Since such changes of pH corresponding to each reaction step cause generation of comparable amounts of salt in the reaction mixture during each pH-adjusting step, a step of removing salt is required by a proper method such as ion-exchange resin. By contrast, use of the membrane-bound D-mannose isomerase enables saccharification in acidic region followed by the direct isomerization reaction with little change of reaction pH, and thus allows no generation of salt.

The optimal temperature of the D-mannose isomerase is 35-65° C., preferably 40-60° C., and more preferably 45-55° C. under the reaction condition at pH 6.0 for 30 minutes.

The D-mannose isomerase is an enzyme composing of four identical subunits of about 45 kDa as measured by SDS-PAGE analysis and gel filtration.

Examples of the acetic acid bacteria herein can include acetic acid bacteria belong to the genera of *Acetobacter, Gluconobacter, Gluconacetobacter, Acidomonas, Asaia, Kozakia, Saccharibacter, Granulibacter, Komagataeibacter, Endobacter*, and *Bombella*, and preferred are acetic acid bacteria belong to the genera of *Acetobacter, Gluconobacter*, or *Gluconacetobacter*.

Examples of acetic acid bacteria belong to the genera of *Acetobacter* can include *Acetobacter pasteurianus, Acetobacter aceti*, and *Acetobacter altoacetigenes.*

Examples of acetic acid bacteria belong to the genera of *Gluconobacter* can include *Gluconobacter thailandicus, Gluconobacter oxydans, Gluconobacter sphaericus, Gluconobacter cerinus, Gluconobacter frateurii*, and *Gluconobacter asaii.*

Examples of acetic acid bacteria belong to the genera of *Gluconacetobacter* can include *Gluconacetobacter intermedius, Gluconacetobacter xylinus, Gluconacetobacter europaeus, Gluconacetobacter diazotrophicus, Gluconacetobacter entanii*, and *Gluconacetobacter liquefaciens.*
(Immobilized Enzyme)

The membrane-bound D-mannose isomerase in the present invention may be immobilized to a carrier to form an immobilized enzyme. As a carrier to be immobilized, any carrier can be used as long as it is used for immobilization of microorganisms or an enzyme. Example thereof can include polysaccharides such as alginic acid, k-carrageenan, cellulose, dextran, chitosan, and agarose; inorganic carriers such as cerite, diatomaceous earth, kaolinite, silica gels, molecular sieve, porous glass, active carbon, calcium carbonate, and ceramics; organic polymers such as ceramics powder, polyvinyl alcohol, polypropylene, acrylamide, ion-exchange resin, hydrophobic adsorption resin, chelating resin, and synthetic adsorption resin; and active carbon, and these may be used in combination. Examples of a method of immobilizing microorganisms (cells), an enzyme or the like to the carrier described above can include known methods such as gel immobilization, adsorption, ionic binding, covalent binding, biochemical specific binding. In addition, examples of the shape of the carriers include a gel shape, a powder shape, and a fiber shape.

Since the membrane-bound D-mannose isomerase is being membrane-bound, cultured cells of the acetic acid bacteria can be directly used as D-mannose isomerase, or a membrane fraction prepared from the acetic acid bacteria can be used as appropriate. A solubilized membrane-bound D-mannose isomerase obtained from the cytoplasmic membrane of the acetic acid bacteria or a purified material obtained from a solubilized membrane-bound D-mannose isomerase can also be used. Description will be made later for the method of providing a membrane fraction, a method of solubilization from the cytoplasmic membrane, and a method of purifying a solubilized enzyme. Note that herein, an immobilized enzyme where the acetic acid bacteria itself is immobilized to the aforementioned carrier as the membrane-bound D-mannose isomerase in the present invention can also be referred to as "immobilized cell".

(Production Method of Membrane-Bound D-mannose Isomerase)

In the method of producing the membrane-bound D-mannose isomerase, a membrane-bound D-mannose isomerase can be produced by providing bacterial cells, or preparing a cytoplasmic membrane fraction from bacterial cells. Since the membrane-bound D-mannose isomerase is bound to the cytoplasmic membrane as described above, bacterial cells themselves or the cytoplasmic membrane fraction can be regarded as a membrane-bound catalyst. D-mannose isomerase acting on D-mannose yielding D-fructose without cell disruption. Examples of a method for providing bacterial cells include centrifugation or filtration.

As a nutrition medium to culture the acetic acid bacteria, a known medium capable of culturing the acetic acid bacteria can be used. Examples thereof include a medium of yeast extract and peptone supplemented with sugars such as D-glucose, D-fructose, or molasses; alcohols such as ethanol, n-propanol, or n-butanol; glycerol; or sodium D-gluconate. The bacterial cultivation can be done by liquid culture under aerobic condition such as shaking culture. Furthermore, aeration can also be supplied. Cells were collected by filtering, centrifugation, or otherwise collecting bacterial cells. Examples of a condition for culturing the acetic acid bacteria can include a condition at 25-35° C. for 36-48 hours.

As a method for providing the cytoplasmic membrane fraction of the acetic acid bacteria, a known method can be used. Examples thereof include a method of suspending cells in a prescribed buffer, physically disrupting them with a French press, a bead homogenizer, a sonicator, glass beads or the like, centrifuging them at 4000 rpm to recover a supernatant and thereby removing undisrupted cells, then subjecting the supernatant thus obtained to ultracentrifugation at 40000 rpm to recover the supernatant, and thereby removing a cytoplasmic fraction to provide a precipitate as the cytoplasmic membrane fraction.

The membrane-bound D-mannose isomerase may also be solubilized from the cytoplasmic membrane and used. As a method of solubilization, a known technique can be used, and examples thereof can include a method of preparing the cytoplasmic membrane fraction obtained from disrupted bacterial cell materials or bacterial cells, separating and solubilizing the isomerase from the cytoplasmic membrane by treatment with a non-ionic surfactant, sonication, chemical treatment with ethylenediamine tetraacetic acid (EDTA), KCl, etc. The solubilized enzyme may further be purified by chromatography such as ion-exchange chromatography or gel filtration chromatography, centrifugation or another technique.

(Production Method of D-Fructose)

The production method of D-fructose just has to cause the membrane-bound D-mannose isomerase or the immobilized enzyme to act on D-mannose solution in the presence of buffer of pH 5.0-6.5. The type of the solution and reaction conditions such as reaction time and reaction temperature can be appropriately selected for the optimal conditions by preliminarily confirming production of D-fructose by paper chromatography or another method. For example, D-fructose can be produced by the cytoplasmic membrane fraction with a membrane concentration of 10-20 mg/mL, and adding D-mannose to the fraction in acetate buffer with pH 5.0-6.5 (10-100 mM), followed by static reaction or gently stirring reaction, e.g., with stirring at 50-80 rpm, at 40-65° C. for several hours to two overnights.

D-mannose and D-fructose may be separated from the reaction mixture thus obtained by column chromatography or another technique, and such a method can increase the concentration of D-fructose. Additionally, in the aforementioned description, D-fructose can be separated from the reaction mixture, and then the remaining unreacted D-mannose may be reused as a substrate in the next batch for D-fructose production.

The present invention will now be specifically described below with reference to the examples, but the technical scope of the present invention is not limited to these examples.

[Example 1] Localization of D-mannose Isomerase

Conventional carbohydrate isomerases are known to be localized in the cytoplasm. Then, localization of the D-mannose isomerase of acetic acid bacteria was examined. As the enzymes, cells, cytoplasmic membrane fraction, cytoplasmic fraction, and a solubilized enzyme obtained from the cytoplasmic membrane fraction were used.

"Cells" were prepared as follows. The acetic acid bacteria, *Gluconobacter thailandicus* NBRC 3257, was cultured until the stationary phase (for about 36 to 40 hours) in a medium containing 2% Na-gluconate, 0.5% D-glucose, 0.3% yeast extract, 0.2% peptone, and 0.3% glycerol. The culture broth thus obtained (350-400 by a Klett photometer) was centrifuged and the cells were collected, washed with 0.01 M acetate buffer (pH 6.0), and further suspended in 0.01 M acetate buffer (pH 6.0), thereby providing "cells".

"Cytoplasmic membrane fraction" was prepared as follows. First, the cells were passed through a French press cell disrupter (Amicon®) to destroy the cells, centrifuged at 4000 rpm for about 10 minutes to separate undisrupted cells (precipitate) from disrupted cytoplasmic membrane fragments and the cytoplasm (supernatant) and recover the supernatant, thereby removing the undisrupted cells. Then, ultracentrifugation was carried out at 40000 rpm for about 60 minutes to separate the cytoplasmic membrane fraction (precipitate) from the cytoplasmic fraction (supernatant) and remove the supernatant, thereby removing the cytoplasm. The precipitate was further suspended in 0.01 M acetate buffer (pH 6.0) and homogenized, and adjusted to 30 mg/mL, thereby providing the cytoplasmic membrane fraction.

As "cytoplasmic fraction", the supernatant fraction after ultracentrifugation was used.

"Solubilized enzyme from the cytoplasmic membrane fraction" was prepared as follows. First, 1.0% (v/v) surfactant Mydol 10 (Kao Corporation) was added to the cytoplasmic membrane fraction (30 mg/mL), and gently stirred at 4° C. overnight. Subsequently, ultracentrifugation was carried out at 40000 rpm for about 60 minutes to separate the solubilized enzyme fraction (supernatant) from the cytoplasmic membrane residual fraction (precipitate), followed by recovery of the supernatant, thereby providing a solubilized enzyme from the cytoplasmic membrane fraction.

Each of the cells, the cytoplasmic membrane fraction, the cytoplasmic fraction, and the solubilized enzyme from the cytoplasmic membrane fraction was reacted with 0.5 M D-mannose as a substrate in 0.1 M acetate buffer (pH 6.0) at room temperature (20-25° C.) for 18 hours. Then, the reacted solution was subjected to thin-layer chromatography (TLC) analysis. Color development was performed using triphenyl tetrazolium chloride. The results are shown in FIG. 1. FIG. 1 shows the lane F for standard D-fructose, lane 1 for the reaction mixture of the cells and D-mannose, lane 2 for the reaction mixture of the cytoplasmic membrane fraction and D-mannose, lane 3 for the reaction mixture of the cytoplasmic fraction and D-mannose, and lane 4 for the reaction mixture of the solubilized enzyme from the cytoplasmic membrane fraction and D-mannose. As shown in FIG. 1, the cells, the cytoplasmic membrane fraction, and the solubilized enzyme from the cytoplasmic membrane fraction generated D-fructose, but the reaction mixture of cytoplasmic fraction with D-mannose generated no D-fructose. This confirmed that the membrane-bound D-mannose isomerase is a membrane-bound, i.e., an enzyme that bounds to the cytoplasmic membrane and functions in the periplasmic space of the cells. Conventional known isomerases derived from bacteria are exclusively present in the cytoplasm thus require disrupting of cells. But the membrane-bound D-mannose isomerase is a membrane-bound itself and thus can be utilized as the enzyme directly without cell disruption.

[Example 2] Generation of D-mannose Isomerase

Culture media containing four different sugars were used to examine which sugar could induce the membrane-bound D-mannose isomerase.

The acetic acid bacteria, *Gluconobacter thailandicus* NBRC 3257, was cultured for 45 hours in media 1-4 described in Table 1. After culturing, the pH of each medium was measured, and cells are collected by centrifugation at 8000 rpm for 10 minutes, washed with 0.01 M acetate buffer (pH 6.0), and passed through a French press cell disrupter (Amicon®) to destroy the cells, followed by preparation of the cytoplasmic membrane fraction in the same method as in Example 1.

TABLE 1

| Medium 1 | 0.5% D-glucose, 2.0% Na-D-gluconate, 0.3% yeast extract, 0.2% peptone |
| Medium 2 | 1% D-mannose, 0.3% yeast extract, 0.2% peptone |
| Medium 3 | 1% D-fructose, 0.3% yeast extract, 0.2% peptone |
| Medium 4 | 1% D-sorbitol, 0.3% yeast extract, 0.2% peptone |

An aliquot of the cytoplasmic membrane fraction (5 mg/mL) was gently reacted with 5 mL of 0.1 M acetate buffer (pH 6.0) containing D-mannose (at the final concentration of 0.1 M) at room temperature at 50 rpm for about 3 hours.

Enzyme activity was assessed by quantifying D-fructose formed using the D-fructose dehydrogenase (FDH) obtained according to the method of Ameyama et al. (Ameyama et al., J. Bacteriol, 145, 814-23, 1981). This is evaluated as the best enzyme for micro-quantification of D-fructose. First, the reaction mixture of the cytoplasmic membrane fraction and D-mannose was treated with trichloroacetic acid to remove proteins as a precipitate, and 50 μL of the supernatant was added with 0.5 mL of acetate buffer (pH 4.5) and 1 unit of D-fructose dehydrogenase (FDH) to provide the total volume of 0.9 mL. A solution, 0.1 mL, of 0.1 M K-ferricyanide was added to start the reaction. After the reaction, 0.5 mL of Dupanol reagent was added to terminate the reaction, followed by addition of 3.5 mL of water, and after 20 minutes, absorbance was measured at 660 nm. Under these conditions, absorbance 4.0 corresponds to 1 μmol of D-fructose (F) corresponding to 180 μg (herein F represents D-fructose). The amount of the membrane-bound D-mannose isomerase that catalyzes generation of 1 μmol D-fructose per min was defined as 1 unit.

Table 2 shows the growth of acetic acid bacteria, pH of the cultured medium, and the intensity of the membrane-bound D-mannose isomerase. The growth extent by turbidity and pH of the culture medium were measured after 45 hours cultivation. The absorbance at 660 nm of the reaction mixture was measured by D-fructose dehydrogenase (FDH) after reaction of 5 mg of the cytoplasmic membrane fraction with D-mannose.

TABLE 2

| | Turbidity | pH | E660 nm/5 mg of cytoplasmic membrane fraction |
|---|---|---|---|
| Medium 1 | 362 | 4.4 | 0.429 (=2.14 μmol F) |
| Medium 2 | 82 | 4.6 | 0.255 (=1.27 μmol F) |
| Medium 3 | 495 | 4.6 | 0.408 (=2.04 μmol F) |
| Medium 4 | 550 | 4.8 | 0.426 (=2.13 μmol F) |

As shown in the results in Table 2, D-mannose isomerase activity was observed in the same level when cultured on D-glucose, D-mannose, D-fructose, and D-sorbitol as a carbon source. This revealed that the membrane-bound D-mannose isomerase is not generated inducively by a specific substrate, but is generated universally in the cytoplasmic membrane of the acetic acid bacteria as long as the acetic acid bacteria is grown. In this point, the membrane-bound D-mannose isomerase is different from conventional pentose (xylose) isomerases, which require a specific inducer, substrate substrate (Patrick J., Lee N., Methods in Enzymol., 41, 453-458 (1975), Yamanaka K., Methods in Enzymol., 41, 459-461 (1975), Yamanaka K., Izumori K., Methods in Enzymol., 41, 462-465 (1975), and Yamanaka K., Methods in Enzymol., 41, 466-471 (1975)).

[Example 3] Distribution of D-mannose Isomerase Activity in Acetic Acid Bacteria The Examples 1 and 2 employed *Gluconobacter thailandicus* NBRC 3257 as the acetic acid bacteria. In this example, D-mannose isomerase activity distributed over the genera of acetic acid bacteria examined.

A culture broth was obtained from stationary-phase culture in a medium containing 2% sorbitol and 0.3% yeast extract. The growth extent was measured by the absorbance at 600 nm, and diluted with water so as to make the absorbance to 0.7, thereby preparing cells. To 0.5 mL of the cells, 0.1 mL of 0.5 M D-mannose and 0.4 mL of 0.2 M acetate buffer (pH 6.0) were added to prepare the reaction mixture and incubated. Then 10 μL of the reaction mixture was reacted with 3 units of D-fructose dehydrogenase in the same manner as in Example 2, and measured the intensity of the reaction mixture by the absorbance at 660 nm. Table 3 shows the results of absorbance at 600 nm after culture indicating the degree of growth of a bacterial species used, and D-fructose formation was measured at 660 nm after the reaction.

TABLE 3

| Acetic acid bacteria | Growth E600 nm | FDH, 660 nm |
|---|---|---|
| *Gluconobacter oxydans* NBRC 3272 | 3.35 | 0.181 |
| *Gluconobacter thailandicus* NBRC 3257 | 2.54 | 0.205 |
| *Gluconobacter oxydans* NBRC 3292 | 3.37 | 0.152 |
| *Gluconobacter frateurii* NBRC 3285 | 2.52 | 0.181 |
| *Gluconobacter frateurii* NBRC 3286 | 3.02 | 0.154 |
| *Gluconobacter frateurii* NBRC 3271 | 3.65 | 0.164 |
| *Gluconobacter oxydans* NBRC 3294 | 2.88 | 0.194 |
| *Gluconobacter oxydans* NBRC 3293 | 3.01 | 0.251 |
| *Gluconobacter oxydans* NBRC 12528 | 2.95 | 0.488 |
| *Gluconobacter thailandicus* NBRC 3254 | 4.35 | 0.202 |
| *Gluconobacter thailandicus* NBRC 3255 | 2.88 | 0.225 |
| *Gluconobacter thailandicus* NBRC 3256 | 2.94 | 0.326 |
| *Acetobacter pasteurianus* SKU 1108 | 2.34 | 0.227 |
| *Acetobacter lovaniensis* NBRC 3284 | 2.74 | 0.15 |
| *Acetobacter pasteurianus* NBRC 3283 | 3.15 | 0.125 |
| *Gluconobacter frateurii* CHM 1 | 1.42 | 0.991 |
| *Gluconobacter frateurii* CHM 8 | 1.81 | 0.764 |
| *Gluconobacter frateurii* CHM 43 | 4.75 | 0.097 |
| *Gluconobacter thailandicus* NBRC 3257 | 3.12 | 0.231 |
| *Gluconacetobacter liquefaciens* NBRC 113262 | 3.11 | 0.181 |
| *Gluconobacter oxydans* NBRC 3244 | 2.48 | 0.175 |
| *Gluconobacter thailandicus* NBRC 3258 | 5.59 | 0.215 |

As shown in Table 3, the intensity of D-mannose isomerase activity was observed in all of the acetic acid bacteria over the genera of *Gluconobacter, Acetobacter*, and *Gluconacetobacter*. This revealed that D-mannose isomerase is distributed in the cytoplasmic membrane in a wide range of acetic acid bacteria.

[Example 4] Purification of D-mannose Isomerase

*Gluconobacter thailandicus* NBRC 3257 was cultured in the method described in Example 1. The D-mannose isomerase was solubilized from the cytoplasmic membrane in the presence of 2% Mydol 10 and 2 M KCl. The solubilized enzyme was put in a dialysis membrane and embedded into powdered sugar overnight to concentrate the enzyme solution. This was subjected to dialysis against 2 mM phosphate buffer (pH 6.0) containing 0.1% Mydol 10 (three times changes with 3 L fresh buffer). After dialysis, the supernatant from which insoluble substances were removed by centrifugation was added to a DEAE-cellulose column (2.5×20 cm) equilibrated with 2 mM phosphate buffer (pH 6.0) containing 0.1% Mydol 10 to adsorb the D-mannose isomerase. The column was washed with the same buffer, and then the D-mannose isomerase was eluted from the column with the same buffer containing 0.3 M KCl. The eluted D-mannose isomerase was subjected to the same operation (concentration with powdered sugar) to provide the concentrated enzyme solution. The enzyme solution was adsorbed to a hydroxyapatite column (3×5 cm) equilibrated with 1 mM phosphate buffer (pH 6.0) containing 0.1%

Mydol 10. Most of contaminated impurities were passed through the column. The D-mannose isomerase was eluted from the column with a phosphate buffer of 0.1 M containing 1% Mydol 10. To this, ammonium sulfate was added up to 65% saturation (430 g of ammonium sulfate/L), and the D-mannose isomerase was collected as a precipitate after centrifugation. The precipitate was dissolved in a small volume of 2 mM phosphate buffer (pH 6.0) containing 0.1% Mydol 10, and fractionated by a Sephadex G-200 column (1×125 cm) equilibrated with the same buffer. Almost complete purification of the D-mannose isomerase was realized throughout the purification steps described above.

FIG. 2 shows the results of measuring molecular mass of the purified D-mannose isomerase by SDS-PAGE. The D-mannose isomerase gave a single stained band at the molecular mass of 45 kDa.

Subsequently, the molecular mass of the D-mannose isomerase was obtained with gel filtration by the method described below. First, a glass column (1.2×120 cm) filled with Sephadex G-200 as a gel filtration agent was equilibrated with 10 mM acetate buffer (pH 6.0) containing 0.1% Mydol 10. Then, a sample solution (0.3 mL) containing the standard marker proteins and Blue Dextran was applied to the column. In addition to the purified D-mannose isomerase, catalase (230 kDa), NADP-GDH (150 kDa), serum albumin dimer (BSA-dimer: 130 kDa), and Blue Dextran (2 MDa) were involved, and fractionated by 150 drops (about 1.8 mL). As a result, the column eluted blue dextran at the 23rd fraction, catalase at the 28th fraction, the purified D-mannose isomerase at the 31st fraction, NADP-GDH at the 36th fraction, and serum albumin dimer (BSA-dimer) at the 38th fraction. The eluted position of Blue Dextran was defined as the void volume (Vo), and the eluted position of the standard proteins (Ve) was used to calculated Ve/Vo. Plotting the Ve/Vo on the longitudinal and the logarithm of molecular mass of each standard substance on the abscissa resulted in almost straight line (FIG. 3). On the basis of the graph in FIG. 3, the purified D-mannose isomerase had the Ve/Vo of 1.45, and thus is estimated to have a molecular mass of 180-190 kDa.

The molecular mass of the D-mannose isomerase in the cytoplasmic membrane was not measured directly, but the results of SDS-PAGE and gel filtration provide estimation that the D-mannose isomerase is composed of four identical subunits of 45-46 kDa, having the N-terminal amino acid sequence of M-S-D-R-L-S- and has the total molecular mass of 180-190 kDa. Note that the purified enzyme also had a purity of almost 100%, as suggested from FIG. 2.

[Example 5] Optimal pH of D-mannose Isomerase

The optimal pH of the D-mannose isomerase was examined. A mixture of 0.1 mL of McIlvaine buffer (pH 3.0, 3.5, 4.0, 4.5, 5.0, 5.5, 6.0, 6.5, 7.0), 0.05 mL of 0.5 M D-mannose, 20 μL of the cytoplasmic membrane fraction prepared in Example 1 or the purified enzyme prepared in Example 4 was used and added with water so as to provide the total volume of 0.2 mL, then gently stirred and reacted at 50° C. After addition of 5 μL of 100% trichloroacetic acid and centrifugation, the supernatant (e.g., 50 μL) was used to examine D-fructose production by measuring the absorbance at 660 nm in accordance with Example 2. The results are shown in FIG. 4. In the figure, closed circles indicate the use of the cytoplasmic membrane fraction, and open circles indicate the use of purified enzyme.

As shown in FIG. 4, it was revealed that the optimal pH of the D-mannose isomerase is found at 5.0 to 6.5 in both of the cytoplasmic membrane fraction and the purified enzyme. Generally, an aqueous sugar solution is sensitive and becomes labile in alkaline and generates colored substances in alkaline. Thus it is not suitable for the production of isomerized sugar. Use of the D-mannose isomerase, on the other hand, to produce isomerized sugar at acidic pH such as pH 5.0-6.5 all the way, and thus enables least generation of colored by-products.

[Example 6] Optimal Temperature of D-mannose Isomerase

The optimal temperature of the D-mannose isomerase was examined. A mixture of 0.1 M acetate buffer (pH 6.0), 0.05 mL of 0.5 M D-mannose, 20 μL of the cytoplasmic membrane fraction prepared in Example 1 or the purified enzyme prepared in Example 4 was used and added with water so as to provide the total volume of 0.2 mL, then gently stirred and reacted at 30° C., 35° C., 40° C., 45° C., 50° C., 55° C., 60° C., 65° C., 70° C. and 75° C. for 30 minutes. After addition of 5 μL of 100% trichloroacetic acid and centrifugation, the supernatant (e.g., 50 μL) was used to examine D-fructose production by measuring the absorbance at 660 nm in accordance with Example 2. The results are shown in FIG. 5. In the figure, closed circles indicate the use of the cytoplasmic membrane fraction, closed rhombuses indicate the use of the purified enzyme, the left ordinate represents OD660 nm in the use of cytoplasmic membrane fraction, and the right ordinate represents OD660 nm in the use of purified enzyme.

As shown in FIG. 5, it was revealed that the optimal temperature of the D-mannose isomerase is found at 40-60° C. Meanwhile, conventional carbohydrate isomerases are known to have the optimal pH of 8.0-9.0, and require substrate for enzyme induction and metalic ions for enzyme formation (Patrick J., Lee N., Methods in Enzymol., 41, 453-458 (1975); Yamanaka K., Methods in Enzymol., 41, 459-461 (1975); Yamanaka K, Izumori K., Methods in Enzymol., 41, 462-465 (1975); and Yamanaka K., Methods in Enzymol., 41, 466-471 (1975)) By contrast, the results in FIGS. 4 and 5 show that the D-mannose isomerase show enzyme activity in acidic pH, maintains the enzyme activity even at 70° C., also does not require any metal ions such as manganese. Thus it has a merit of being capable of stably promoting the isomerization reaction under a wide range of conditions.

[Example 7] Substrate Specificity of D-Mannose Isomerase

The purified enzyme produced in Example 4 was used to examine the substrate specificity of the D-mannose isomerase. C5 sugars such as D-xylose, D-arabinose, and D-ribulose, and C6 sugars such as D-glucose, D-mannose, and D-galactose were used as substrates, reacted with the purified enzyme, and examined for isomerized products by TLC. Note that via isomerization, D-xylose and D-arabinose generate D-xylulose and D-ribulose, respectively. Additionally, via isomerization, D-mannose and D-galactose generate D-fructose and D-tagatose, respectively. FIGS. 6 and 7 show the results of each TLC. Color development was performed with triphenyl tetrazolium chloride.

First, lanes 1-3 in FIG. 6 confirmed that the D-D-mannose isomerase did not generate D-xylulose from D-xylose. Then, lanes 4-6 in FIG. 6 confirmed that the D-mannose isomerase did not generate D-ribulose from D-arabinose. Furthermore, lanes 7 and 8 in FIG. 6 confirmed that the D-mannose isomerase did not exhibit any change with D-ribose.

Next, lanes 1-3 in FIG. 7 confirmed that the membrane-bound D-mannose isomerase did not exhibit any spot of D-tagatose, when incubated with D-galactose. Then, lanes 3-5 in FIG. 7 confirmed that the D-mannose isomerase reacted with D-mannose to generate D-fructose. Furthermore, lanes 6-8 in FIG. 7 confirmed that the D-mannose isomerase did not generate D-tagatose and not reacted with D-galactose. In lane 5, standard D-mannose provides no spot image in FIG. 7, because triphenyl tetrazolium chloride used did not clearly develop color, but a vague shade was visually confirmed.

The results in FIGS. 6 and 7 confirmed that the D-mannose isomerase has high substrate specificity to D-mannose. Whereas FIGS. 6 and 7 show results in use of the purified enzyme prepared in Example 4, the cytoplasmic membrane fraction also exhibited the same results as in the purified enzyme in TLC analysis in the same manner (not depicted).

[Example 8] Reaction Equilibrium and Km Value

Assay for reaction equilibrium was carried out with 0.2 M acetate buffer (pH 6.0). D-Fructose was produced from D-mannose as a substrate and the cytoplasmic membrane fraction according to Example 1, and quantified using FDH in the same manner as in Example 2. In addition, D-mannose was produced by isomerization using D-fructose as a substrate and the enzyme, and quantified by the method using D-glucose dehydrogenase that has NADP-dependency and reacts only to D-glucose and D-mannose (Adachi et al., Agric. Biol. Chem., 44, 301-308(1980)). The results showed that the conversion of D-mannose to D-fructose was 75%, and the conversion of D-fructose to D-mannose was 22-25%. Furthermore, the D-mannose isomerase showed Km value of 75 mM for D-mannose in either use of the membrane fraction or the purified enzyme.

[Example 9] Reaction to a Mixture of D-mannose and D-glucose

The inventors previously disclosed a method of hydrolyzing a konjac taro to provide konjac taro hydrolyzed solution containing D-mannose and D-glucose as main sugar components (Patent Literature 1). The konjac taro hydrolyzed solution thus obtained by the method (with a sugar concentration of 19% consisting of 10% D-mannose/9% D-glucose (by HPLC analysis)) was treated with ion-exchange resin such as Amberlite™ to remove polyphenolic substances. It was subjected as a substrate to the action of the D-mannose isomerase in 0.1 M acetate buffer (pH 6.0) at 50° C. for 3 days. Consequently, D-mannose was converted to D-fructose with a conversion rate of 80%. This result revealed that the D-mannose isomerase is capable of isomerizing D-mannose even in the presence of high concentration of D-glucose. Furthermore, use of the method of providing a konjac taro hydrolyzed solution and the D-mannose isomerase allows further application of konjac taro to the food industry. Particularly, production of mixed solution of D-fructose and D-glucose by hydrolyzing a konjac taro to provide a sugar solution containing D-mannose and D-glucose, and further isomerizing D-mannose to D-fructose. Moreover, the present invention uses acetic acid bacteria that are familiar our traditional brewing industries. Thus, it is accompanied with sufficient long history of eating experience. Therefore, the present invention can be considered as a method with high safety.

[Example 10] Immobilization of Cells and Isomerization of D-mannose by Immobilized Cells For the purpose of industrial utilization of the D-mannose isomerase, immobilization was investigated. *Gluconobacter thailandicus* NBRC 3257 cells was suspended in 10 mM acetate buffer (pH 6.0) to about 200 mg/mL. Meanwhile, 2% sodium alginate (Na-alginate) was prepared and mixed so as to provide the cell suspension: sodium alginate=1:3. The mixture was dropped into a 5% calcium chloride solution from a thin nozzle using a Perista® pump. The cells were immobilized to calcium-alginate gel with stirring. After stirring for several hours, the beads were transferred to 10 mM acetate buffer (pH 6.0) to remove calcium chloride. The 10 mM acetate buffer (pH 6.0) was replaced at least three times. FIG. 8 shows a photo of the immobilized cells thus obtained.

In FIG. 8, the left panel represents a photo of the immobilized cells just after preparation. The right panel represents a photo of dried immobilized cells prepared after leaving them for 2-3 days dehydration over silica gels particles under reduced pressure. Furthermore, when the dried immobilized cells were resuspended in an appropriate amount of water and reacted with D-mannose, generation of D-fructose could be confirmed. Accordingly, such immobilized cells are capable of recovering as immobilized cells having the enzyme activity with little loss of the enzyme activity, by storage in a desiccator with silica gels when not in use.

[Example 11] Reaction of Mixture of D-mannose and D-glucose Using Immobilized Cells The dried immobilized cells provided in Example 10 was used and reacted with a mixture of D-mannose and D-glucose to attempt production of D-fructose.

In an airtight container, 5 mg of the dried immobilized cells provided in Example 10, (1) 0.5 M D-mannose, (2) 0.5 M D-mannose+0.5 M D-glucose, (3) 0.5 M D-mannose+0.5 M D-fructose were charged, adjusted with 0.2 M acetate buffer (pH 5.0) so as to provide a total volume of 3.5 mL, and incubated at 50° C. for 3 days. The results are shown in Table 4.

TABLE 4

| | Post-reaction concentration of D-fructose | | |
|---|---|---|---|
| Initial concentration | Day 1 | Day 2 | Day 3 |
| 0.5M D-mannose | 0.337M | 0.392M | 0.411M |
| 0.5M D-mannose + 0.5M D-glucose | 0.365M | 0.415M | 0.455M |
| 0.5M D-mannose + 0.5M D-fructose | 0.795M | 0.896M | 0.899M |

As can be seen in the results in Table 4, about 80% or more of D-mannose added was converted to D-fructose within 2 days, and the reaction came to the equilibrium. Additionally, conventional known isomerases are known to include enzymes that is prevented to react by presence of a prescribed sugar such as D-glucose or a sugar to be the product. However, the results in Table 4 confirmed that even use of reaction mixture containing, in addition to D-mannose, D-glucose or the product D-fructose does not affect conversion of D-mannose to D-fructose by the dried immobilized cells. Additionally, the amount of D-fructose stayed unchanged from day 2 to day 3 of the reaction, and thus the isomerization reaction by the dried immobilized cells can be considered to be terminated. Furthermore, it was suggested that since conversion of D-mannose to D-fructose proceeds even in co-presence of D-mannose and D-fructose. It is possible to isolate fructose formed from the reaction mixture and reuse the remaining solution (the solution still contained certain amount of D-fructose) can be used as substrate for the next batch, thus leading to improved production efficiency of D-fructose.

Next, instead of D-mannose, a konjac taro hydrolyzed solution was used to react with the dried immobilized cells in the same manner as described above. In detail, the konjac taro hydrolyzed solution provided in Example 9 (with a final concentration of 205 mg/mL or 150 mg/mL as the content of sugar) and 5 mg of the dried immobilized cells provided in Example 10 were charged into an airtight container, adjusted with 0.2 M acetate buffer (pH 5.0) so as to provide the total volume of 3.5 mL, and kept the reaction at 50° C. for about 3 days. The results are shown in Table 5. Note that a konjac taro hydrolyzed solution contained D-glucose and D-mannose at the proportion of about 1:1.5.

TABLE 5

| Initial concentration | Post-reaction concentration | | |
|---|---|---|---|
| of sugar | Day 1 | Day 2 | Day 3 |
| 205 mg of sugar/mL | 72 mg/mL | 107 mg/mL | 108 mg/mL |
| 150 mg of sugar/mL | 54 mg/mL | 72 mg/mL | 82 mg/mL |

As can be seen in the results in Table 5, D-fructose was also generated from D-mannose from the konjac taro hydrolyzed solution by the dried immobilized cells, and the reaction to D-fructose almost reached equilibrium after 2 days reaction.

INDUSTRIAL APPLICABILITY

The present invention allows processing konjac taro, which had a difficulty in conversion to a nutritious food resource, into a carbohydrate resource comparable with sugar cane, sugar beet, or the like. Thus is can be utilized in the sugar production industry, the food-processing industry, and the food manufacturing industry.

The invention claimed is:

1. An isolated D-mannose isomerase bound to a cytoplasmic membrane of acetic acid bacteria,
   wherein the acetic acid bacteria belong to genera of *Acetobacter, Gluconobacter*, or *Gluconacetobacter.*

2. The D-mannose isomerase according to claim 1 having the following characteristics (a)-(c):
   (a) acting on D-mannose to generate D-fructose;
   (b) having the optimal reaction pH of 5.0-6.5 under an enzymatic reaction condition at 50° C.; and
   (c) having the optimal reaction temperature of 40-65° C. under the reaction condition at pH 6.0 for 30 minutes.

3. An immobilized enzyme comprising the isolated D-mannose isomerase according to claim 1 immobilized to a carrier.

4. A method of producing an isolated D-mannose isomerase bound to a cytoplasmic membrane of acetic acid bacteria comprising:
   (a) culturing acetic acid bacteria in a nutrition medium to obtain bacterial cells; and
   (b) isolating the membrane-bound D-mannose isomerase from said bacterial cells by preparing a cytoplasmic membrane fraction from the bacterial cells, wherein the acetic acid bacteria belong to genera of *Acetobacter, Gluconobacter*, or *Gluconacetobacter.*

5. A method of producing D-fructose comprising contacting a D-mannose solution with the D-mannose isomerase according to claim 1.

6. An immobilized enzyme, in which the D-mannose isomerase of claim 2 is immobilized on a carrier.

7. An immobilized enzyme, in which the D-mannose isomerase of claim 1 is immobilized on a carrier.

8. A method for producing D-fructose, comprising allowing the D-mannose isomerase of claim 2 to act on a solution containing D-mannose.

9. A method for producing D-fructose, comprising allowing the immobilized enzyme of claim 3 to act on a solution containing D-mannose.

10. A method for producing D-fructose, comprising allowing the D-mannose isomerase of claim 1 to act on a D-mannose solution.

11. A method for producing D-fructose, comprising allowing the immobilized enzyme of claim 3 to act on a solution containing D-mannose.

12. The isolated D-mannose isomerase according to claim 1, wherein the acetic acid bacteria belong to a species selected from the group consisting of *Acetobacter pasteurianus, Acetobacter aceti, Acetobacter altoacetigenes, Gluconobacter thailandicus, Gluconobacter oxydans, Gluconobacter sphaericus, Gluconobacter cerinus, Gluconobacter frateurii, Gluconobacter asaii, Gluconacetobacter interme-*

*dius, Gluconacetobacter xylinus, Gluconacetobacter europaeus, Gluconacetobacter diazotrophicus, Gluconacetobacter entanii,* and *Gluconacetobacter liquefaciens.*

13. The isolated D-mannose isomerase according to claim 1, wherein the acetic acid bacteria belong to a species selected from the group consisting of *Acetobacter pasteurianus, Gluconobacter thailandicus, Gluconobacter oxydans, Gluconobacter frateurii,* and *Gluconacetobacter liquefaciens.*

14. The method according to claim 4, wherein the acetic acid bacteria belong to a species selected from the group consisting of *Acetobacter pasteurianus, Acetobacter aceti, Acetobacter altoacetigenes, Gluconobacter thailandicus, Gluconobacter oxydans, Gluconobacter sphaericus, Gluconobacter cerinus, Gluconobacter frateurii, Gluconobacter asaii, Gluconacetobacter intermedius, Gluconacetobacter xylinus, Gluconacetobacter europaeus, Gluconacetobacter diazotrophicus, Gluconacetobacter entanii,* and *Gluconacetobacter liquefaciens.*

15. The method according to claim 4, wherein the acetic acid bacteria belong to a species selected from the group consisting of *Acetobacter pasteurianus, Gluconobacter thailandicus, Gluconobacter oxydans, Gluconobacter frateurii,* and *Gluconacetobacter liquefaciens.*

* * * * *